(12) United States Patent
Mangiardi et al.

(10) Patent No.: US 7,527,644 B2
(45) Date of Patent: May 5, 2009

(54) STENT WITH GEOMETRY DETERMINATED FUNCTIONALITY AND METHOD OF MAKING THE SAME

(75) Inventors: Eric K. Mangiardi, Charlotte, NC (US); Jason M Reynolds, Charlotte, NC (US)

(73) Assignee: Alveolus Inc., Charlotte, NC (US)

( * ) Notice: Subject to any disclaimer, the term of this patent is extended or adjusted under 35 U.S.C. 154(b) by 1 day.

(21) Appl. No.: 10/288,615

(22) Filed: Nov. 5, 2002

(65) Prior Publication Data

US 2004/0088040 A1 May 6, 2004

(51) Int. Cl.
*A61F 2/06* (2006.01)
(52) U.S. Cl. ..................................... 623/1.15
(58) Field of Classification Search ............... 623/1.15, 623/1.16, 1.2, 1.44, 1.46; 606/191–198
See application file for complete search history.

(56) References Cited

U.S. PATENT DOCUMENTS

| | | | |
|---|---|---|---|
| 3,818,511 A | 6/1974 | Goldberg et al. | |
| 4,343,048 A | 8/1982 | Ross et al. | |
| 4,441,215 A | 4/1984 | Kaster | |
| 4,655,771 A | 4/1987 | Wallsten | |
| 4,665,906 A | 5/1987 | Jervis | |
| 4,680,031 A | 7/1987 | Alonso | |
| 4,733,665 A | 3/1988 | Palmaz | |
| 4,739,762 A | 4/1988 | Palmaz | |
| 4,743,251 A | 5/1988 | Barra | |
| 4,800,882 A | 1/1989 | Gianturco | |
| 4,820,262 A | 4/1989 | Finney | |
| 4,820,298 A | 4/1989 | Leveen et al. | |
| 4,856,516 A | 8/1989 | Hillstead | |
| 4,886,062 A | 12/1989 | Wiktor | |
| 5,032,128 A | 7/1991 | Alonso | |
| 5,061,275 A | 10/1991 | Wallsten et al. | |
| 5,064,435 A | 11/1991 | Porter | |
| 5,067,957 A | 11/1991 | Jervis | |
| 5,073,694 A | 12/1991 | Tessier et al. | |
| 5,102,417 A | 4/1992 | Palmaz | |

(Continued)

FOREIGN PATENT DOCUMENTS

CA 2 356 911 A1 7/2000

(Continued)

OTHER PUBLICATIONS

PCT Notification of Transmittal of the International Search Report, PCT International Search Report mailed Jan. 18, 2006 for PCT/US04/31304 (Filed Sep. 24, 2004).

(Continued)

*Primary Examiner*—Kevin T Truong
(74) *Attorney, Agent, or Firm*—Alston & Bird LLP (57) ABSTRACT

The present invention, in an exemplary embodiment, provides a stent, which combines many of the excellent characteristics of both silicone and metal stents while eliminating the undesirable ones. In particular, a principal objective in accordance with the present invention is to provide a family of stents where the relative hardness/softness of regions of the stent can differ from other regions of the stent to provide additional patient comfort and resistance to radial forces. An exemplary embodiment also provides a family of stents with novel interstice configurations that facilitate flexibility, durability and/or proper installation.

38 Claims, 4 Drawing Sheets

U.S. PATENT DOCUMENTS

| | | |
|---|---|---|
| 5,104,404 A | 4/1992 | Wolff |
| 5,190,546 A | 3/1993 | Jervis |
| 5,195,984 A | 3/1993 | Schatz |
| 5,229,431 A | 7/1993 | Pinchuk |
| 5,292,331 A | 3/1994 | Boneau |
| 5,345,057 A | 9/1994 | Muller |
| 5,354,309 A | 10/1994 | Schnepp-Pesch et al. |
| 5,356,423 A | 10/1994 | Tihon et al. |
| 5,383,892 A | 1/1995 | Cardon et al. |
| 5,383,925 A | 1/1995 | Schmitt |
| 5,421,955 A | 6/1995 | Lau et al. |
| 5,433,723 A | 7/1995 | Lindenberg et al. |
| 5,443,498 A | 8/1995 | Fontaine |
| 5,449,373 A | 9/1995 | Pinchasik et al. |
| 5,480,431 A | 1/1996 | Frietag et al. |
| 5,514,154 A | 5/1996 | Lau et al. |
| 5,520,697 A | 5/1996 | Lindenberg et al. |
| 5,534,287 A | 7/1996 | Lukic |
| 5,540,713 A | 7/1996 | Schnepp-Pesch et al. |
| 5,562,725 A | 10/1996 | Schmitt et al. |
| 5,575,818 A | 11/1996 | Pinchuk |
| 5,591,157 A | 1/1997 | Hennings et al. |
| 5,591,197 A | 1/1997 | Orth et al. |
| 5,593,442 A | 1/1997 | Klein |
| 5,597,378 A | 1/1997 | Jervis |
| 5,601,593 A | 2/1997 | Freitag |
| 5,609,629 A | 3/1997 | Fearnot et al. |
| 5,618,301 A | 4/1997 | Hauenstein et al. |
| 5,628,788 A | 5/1997 | Pinchuk |
| 5,643,312 A | 7/1997 | Fischell et al. |
| 5,645,559 A | 7/1997 | Hachtman et al. |
| 5,662,713 A | 9/1997 | Andersen et al. |
| 5,667,486 A | 9/1997 | Mikulich et al. |
| 5,674,241 A | 10/1997 | Bley et al. |
| 5,681,346 A | 10/1997 | Orth et al. |
| 5,697,971 A | 12/1997 | Fischell et al. |
| 5,707,386 A | 1/1998 | Schnepp-Pesch et al. |
| 5,713,949 A | 2/1998 | Jayaraman |
| 5,716,393 A | 2/1998 | Lindenberg et al. |
| 5,725,572 A | 3/1998 | Lam et al. |
| 5,733,303 A | 3/1998 | Israel et al. |
| 5,741,333 A | 4/1998 | Frid |
| 5,755,776 A | 5/1998 | Al-Saadon |
| 5,755,781 A * | 5/1998 | Jayaraman ................. 623/1.16 |
| 5,759,192 A | 6/1998 | Saunders |
| 5,766,238 A | 6/1998 | Lau et al. |
| 5,776,161 A | 7/1998 | Globerman |
| 5,780,807 A | 7/1998 | Saunders |
| 5,807,404 A | 9/1998 | Richter |
| 5,814,063 A | 9/1998 | Freitag |
| 5,824,042 A | 10/1998 | Lombardi et al. |
| 5,827,321 A | 10/1998 | Roubin et al. |
| 5,833,707 A | 11/1998 | McIntyre et al. |
| 5,836,966 A | 11/1998 | St. Germain |
| 5,837,313 A | 11/1998 | Ding et al. |
| 5,843,120 A | 12/1998 | Israel et al. |
| 5,853,419 A | 12/1998 | Imran |
| 5,860,999 A | 1/1999 | Schnepp-Pesch et al. |
| 5,873,904 A | 2/1999 | Ragheb et al. |
| 5,876,418 A | 3/1999 | KarlheinzHauenstein et al. |
| 5,876,445 A | 3/1999 | Anderson et al. |
| 5,876,448 A | 3/1999 | Thompson et al. |
| 5,876,449 A | 3/1999 | Starck et al. |
| 5,879,370 A | 3/1999 | Fischell et al. |
| 5,902,475 A | 5/1999 | Trozera et al. |
| 5,911,732 A | 6/1999 | Hojeibane |
| 5,922,019 A | 7/1999 | Hankh et al. |
| 5,922,020 A | 7/1999 | Klein et al. |
| 5,922,393 A | 7/1999 | Jayaraman |
| 5,931,866 A | 8/1999 | Frantzen |
| 5,935,162 A | 8/1999 | Dang |
| 5,938,682 A | 8/1999 | Hojeibane et al. |
| 5,968,070 A | 10/1999 | Bley et al. |
| 5,968,091 A | 10/1999 | Pinchuk et al. |
| 5,971,950 A | 10/1999 | Lopez et al. |
| 5,972,018 A | 10/1999 | Israel et al. |
| 5,980,552 A | 11/1999 | Pinchasik et al. |
| 6,017,365 A | 1/2000 | Von Oepen |
| 6,022,371 A | 2/2000 | Killion |
| 6,027,527 A | 2/2000 | Asano et al. |
| 6,033,435 A | 3/2000 | Penn et al. |
| 6,042,597 A | 3/2000 | Kveen et al. |
| 6,048,361 A | 4/2000 | Von Oepen |
| 6,051,021 A | 4/2000 | Frid |
| 6,053,941 A | 4/2000 | Lindenberg et al. |
| 6,056,775 A | 5/2000 | Borghi et al. |
| 6,059,811 A | 5/2000 | Pinchasik et al. |
| 6,096,070 A | 8/2000 | Raghed et al. |
| 6,099,650 A | 8/2000 | Penn et al. |
| 6,106,548 A | 8/2000 | Roubin et al. |
| 6,120,534 A | 9/2000 | Ruiz |
| 6,131,266 A | 10/2000 | Saunders |
| 6,132,461 A | 10/2000 | Thompson |
| 6,136,006 A | 10/2000 | Johnson et al. |
| 6,136,022 A | 10/2000 | Nunez et al. |
| 6,146,403 A | 11/2000 | St. Germain |
| 6,146,416 A | 11/2000 | Andersen et al. |
| 6,156,052 A | 12/2000 | Richter et al. |
| 6,159,238 A | 12/2000 | Killion et al. |
| 6,159,239 A | 12/2000 | Greenhalgh |
| 6,171,334 B1 | 1/2001 | Cox |
| 6,174,329 B1 | 1/2001 | Callol et al. |
| 6,179,867 B1 | 1/2001 | Cox |
| 6,183,506 B1 | 2/2001 | Penn et al. |
| 6,190,407 B1 | 2/2001 | Ogle et al. |
| 6,193,744 B1 | 2/2001 | Ehr et al. |
| 6,203,568 B1 | 3/2001 | Lombardi et al. |
| 6,206,916 B1 | 3/2001 | Furst |
| 6,217,608 B1 | 4/2001 | Penn et al. |
| 6,231,598 B1 | 5/2001 | Berry et al. |
| 6,231,599 B1 | 5/2001 | Ley |
| 6,241,760 B1 | 6/2001 | Jang |
| 6,248,058 B1 | 6/2001 | Silverman et al. |
| 6,251,134 B1 | 6/2001 | Alt et al. |
| 6,258,121 B1 * | 7/2001 | Yang et al. ................. 623/1.46 |
| 6,270,524 B1 | 8/2001 | Kim |
| 6,273,910 B1 | 8/2001 | Limon |
| 6,283,992 B1 | 9/2001 | Hankh et al. |
| 6,293,964 B1 | 9/2001 | Yadav |
| 6,293,966 B1 | 9/2001 | Frantzen |
| 6,293,968 B1 | 9/2001 | Taheri |
| 6,306,141 B1 | 10/2001 | Jervis |
| 6,312,459 B1 | 11/2001 | Huang et al. |
| 6,315,794 B1 | 11/2001 | Richter |
| 6,325,821 B1 | 12/2001 | Gaschino et al. |
| 6,325,825 B1 | 12/2001 | Kula et al. |
| 6,336,938 B1 | 1/2002 | Kavteladze et al. |
| 6,348,065 B1 | 2/2002 | Brown et al. |
| 6,352,552 B1 | 3/2002 | Levinson et al. |
| 6,355,063 B1 | 3/2002 | Calcote |
| 6,361,557 B1 | 3/2002 | Gittings et al. |
| 6,375,676 B1 | 4/2002 | Cox |
| 6,375,677 B1 | 4/2002 | Penn et al. |
| 6,380,457 B1 | 4/2002 | Yurek et al. |
| 6,395,020 B1 | 5/2002 | Ley et al. |
| 6,409,750 B1 | 6/2002 | Hyodoh et al. |
| 6,409,754 B1 | 6/2002 | Smith et al. |
| 6,416,538 B1 | 7/2002 | Ley et al. |
| 6,420,378 B1 | 7/2002 | Rubinfeld |
| 6,423,084 B1 | 7/2002 | St. Germain |
| 6,423,091 B1 | 7/2002 | Hojeibane |
| 6,428,570 B1 | 8/2002 | Globerman |
| 6,432,133 B1 | 8/2002 | Lau et al. |
| 6,436,133 B1 | 8/2002 | Furst et al. |

| | | | | | | |
|---|---|---|---|---|---|---|
| 6,440,162 B1 | 8/2002 | Cox et al. | | 6,673,154 B1 | 1/2004 | Pacetti et al. |
| 6,443,982 B1 | 9/2002 | Israel et al. | | 6,676,697 B1 | 1/2004 | Richter |
| 6,451,049 B2 | 9/2002 | Vallana et al. | | 6,679,910 B1 | 1/2004 | Granada |
| 6,461,380 B1 | 10/2002 | Cox | | 6,679,911 B2 | 1/2004 | Burgermeister |
| 6,461,381 B2 | 10/2002 | Israel et al. | | 6,682,554 B2 | 1/2004 | Oepen et al. |
| 6,464,720 B2 | 10/2002 | Boatman et al. | | 6,685,736 B1 | 2/2004 | White et al. |
| 6,464,722 B2 | 10/2002 | Israel et al. | | 6,685,745 B2 | 2/2004 | Reever |
| 6,471,721 B1 | 10/2002 | Dang | | 6,689,158 B1 | 2/2004 | White et al. |
| 6,475,234 B1 | 11/2002 | Richter et al. | | 6,689,162 B1 | 2/2004 | Thompson |
| 6,475,236 B1 | 11/2002 | Roubin et al. | | 6,692,483 B2 | 2/2004 | Vardi et al. |
| 6,478,815 B1 | 11/2002 | Alt | | 6,692,521 B2 | 2/2004 | Pinchasik |
| 6,488,703 B1 | 12/2002 | Kveen et al. | | 6,692,522 B1 | 2/2004 | Richter |
| 6,508,834 B1 | 1/2003 | Pinchasik et al. | | 6,695,833 B1 | 2/2004 | Frantzen |
| 6,514,285 B1 | 2/2003 | Pinchasik | | 6,695,876 B1 | 2/2004 | Marotta et al. |
| 6,533,805 B1 | 3/2003 | Jervis | | 6,699,276 B2 | 3/2004 | Sogard et al. |
| 6,533,810 B2 | 3/2003 | Hankh et al. | | 6,699,278 B2 | 3/2004 | Fischell et al. |
| 6,540,777 B2 | 4/2003 | Stenzel | | 6,706,061 B1 | 3/2004 | Fischell et al. |
| 6,551,351 B2 | 4/2003 | Smith et al. | | 6,706,062 B2 | 3/2004 | Vardi et al. |
| 6,569,194 B1 | 5/2003 | Pelton | | 6,709,440 B2 | 3/2004 | Callol et al. |
| 6,572,646 B1 | 6/2003 | Boylan et al. | | 6,709,451 B1 | 3/2004 | Noble et al. |
| 6,589,276 B2 | 7/2003 | Pinchasik et al. | | 6,709,453 B2 | 3/2004 | Pinchasik et al. |
| 6,602,285 B1 | 8/2003 | Von Oepen et al. | | 6,709,454 B1 | 3/2004 | Cox et al. |
| 6,613,078 B1 | 9/2003 | Barone | | 6,712,843 B2 | 3/2004 | Elliott |
| 6,613,079 B1 | 9/2003 | Wolinsky et al. | | 6,712,844 B2 | 3/2004 | Pacetti |
| 6,613,080 B1 | 9/2003 | Lootz | | 6,712,846 B1 | 3/2004 | Kraus et al. |
| 6,613,081 B2 | 9/2003 | Kim et al. | | 6,716,240 B2 | 4/2004 | Fischell et al. |
| 6,616,688 B2 | 9/2003 | Von Oepen | | 6,719,782 B1 | 4/2004 | Chuter |
| 6,616,689 B1 | 9/2003 | Ainsworth et al. | | 6,719,991 B2 | 4/2004 | Darouiche et al. |
| 6,616,690 B2 | 9/2003 | Rolando et al. | | 6,723,118 B1 | 4/2004 | Ballou et al. |
| 6,620,192 B1 | 9/2003 | Jalisi | | 6,723,119 B2 | 4/2004 | Pinchasik et al. |
| 6,620,193 B1 | 9/2003 | Lau et al. | | 6,723,120 B2 | 4/2004 | Yan |
| 6,620,201 B1 | 9/2003 | Nadal et al. | | 6,723,121 B1 | 4/2004 | Zhong |
| 6,623,518 B2 | 9/2003 | Thompson et al. | | 6,723,373 B1 | 4/2004 | Narayanan et al. |
| 6,623,520 B2 | 9/2003 | Jalisi | | 6,730,064 B2 | 5/2004 | Ragheb et al. |
| 6,629,994 B2 * | 10/2003 | Gomez et al. ............... 623/1.15 | | 6,730,116 B1 | 5/2004 | Wolinsky et al. |
| 6,635,084 B2 | 10/2003 | Israel et al. | | 6,730,117 B1 | 5/2004 | Tseng et al. |
| 6,638,293 B1 | 10/2003 | Makower et al. | | 6,730,120 B2 | 5/2004 | Berg et al. |
| 6,638,300 B1 | 10/2003 | Frantzen | | 6,733,523 B2 | 5/2004 | Shaolian et al. |
| 6,638,302 B1 | 10/2003 | Curcio et al. | | 6,733,524 B2 | 5/2004 | Tseng et al. |
| 6,641,607 B1 | 11/2003 | Hossainy et al. | | 6,736,838 B1 | 5/2004 | Richter |
| 6,641,608 B1 | 11/2003 | Pulnev | | 6,736,843 B1 | 5/2004 | Fariabi |
| 6,641,609 B2 | 11/2003 | Globerman | | 6,736,844 B1 | 5/2004 | Glatt et al. |
| 6,641,611 B2 | 11/2003 | Jayaraman | | 6,740,113 B2 | 5/2004 | Vrba |
| 6,645,240 B2 | 11/2003 | Yec | | 6,740,114 B2 | 5/2004 | Burgermeister |
| 6,645,242 B1 | 11/2003 | Quinn | | 6,740,115 B2 | 5/2004 | Lombardi et al. |
| 6,652,572 B2 | 11/2003 | Kugler et al. | | 6,743,252 B1 | 6/2004 | Bates et al. |
| 6,652,573 B2 | 11/2003 | von Oepen | | 6,746,475 B1 | 6/2004 | Rivelli, Jr. |
| 6,652,575 B2 | 11/2003 | Wang | | 6,746,476 B1 | 6/2004 | Hojeibane |
| 6,652,579 B1 | 11/2003 | Cox et al. | | 6,746,477 B2 | 6/2004 | Moore |
| 6,653,426 B2 | 11/2003 | Alvarado et al. | | 6,746,479 B2 | 6/2004 | Ehr et al. |
| 6,656,201 B2 | 12/2003 | Ferrera et al. | | 6,746,482 B2 | 6/2004 | Ung-Chhun |
| 6,656,214 B1 | 12/2003 | Fogarty et al. | | 6,749,629 B1 | 6/2004 | Hong et al. |
| 6,656,216 B1 | 12/2003 | Hossainy et al. | | 6,752,826 B2 | 6/2004 | Holloway et al. |
| 6,656,217 B1 | 12/2003 | Herzog, Jr. et al. | | 6,752,829 B2 | 6/2004 | Kocur et al. |
| 6,656,220 B1 * | 12/2003 | Gomez et al. ............... 623/1.15 | | 6,753,071 B1 | 6/2004 | Pacetti |
| 6,656,351 B2 | 12/2003 | Boyle | | 6,755,856 B2 | 6/2004 | Fierens et al. |
| 6,660,019 B1 | 12/2003 | Richter et al. | | 6,756,007 B2 | 6/2004 | Pletzer et al. |
| 6,660,030 B2 | 12/2003 | Shaolian et al. | | 6,758,858 B2 | 7/2004 | McCrea et al. |
| 6,660,034 B1 | 12/2003 | Mandrusov et al. | | 6,758,859 B1 | 7/2004 | Dang et al. |
| 6,660,827 B2 | 12/2003 | Loomis et al. | | 6,758,860 B1 | 7/2004 | Penn et al. |
| 6,663,664 B1 | 12/2003 | Pacetti | | 6,761,731 B2 | 7/2004 | Majercak |
| 6,664,335 B2 | 12/2003 | Krishnan | | 6,764,505 B1 | 7/2004 | Hossainy et al. |
| 6,666,881 B1 | 12/2003 | Richter et al. | | 6,764,506 B2 | 7/2004 | Roubin et al. |
| 6,666,884 B1 | 12/2003 | Webster | | 6,764,507 B2 | 7/2004 | Shanley et al. |
| 6,669,721 B1 | 12/2003 | Bose et al. | | 6,764,519 B2 | 7/2004 | Whitmore, III |
| 6,669,722 B2 | 12/2003 | Chen et al. | | 6,770,086 B1 | 8/2004 | Girton |
| 6,669,723 B2 | 12/2003 | Killion et al. | | 6,770,088 B1 | 8/2004 | Jang |
| 6,673,102 B1 | 1/2004 | Vonesh et al. | | 6,770,089 B1 | 8/2004 | Hong et al. |
| 6,673,103 B1 | 1/2004 | Golds et al. | | 6,770,091 B2 | 8/2004 | Richter et al. |
| 6,673,104 B2 | 1/2004 | Barry | | 6,773,445 B2 | 8/2004 | Finlay et al. |
| 6,673,105 B1 | 1/2004 | Chen | | 6,774,157 B2 | 8/2004 | DelMain |
| 6,673,106 B2 | 1/2004 | Mitelberg et al. | | 6,774,278 B1 | 8/2004 | Ragheb et al. |
| 6,673,107 B1 | 1/2004 | Brandt et al. | | 6,776,022 B2 | 8/2004 | Kula et al. |

| Patent/Pub No. | Date | Inventor(s) |
|---|---|---|
| 6,776,792 B1 | 8/2004 | Yan et al. |
| 6,776,793 B2 | 8/2004 | Brown et al. |
| 6,776,794 B1 | 8/2004 | Hong et al. |
| 6,776,795 B2 | 8/2004 | Pelton |
| 6,776,796 B2 | 8/2004 | Falotico et al. |
| 6,786,929 B2 | 9/2004 | Gambale et al. |
| 6,790,222 B2 | 9/2004 | Kugler et al. |
| 6,790,227 B2 | 9/2004 | Burgermeister |
| 6,790,228 B2 | 9/2004 | Hossainy et al. |
| 6,796,997 B1 | 9/2004 | Penn et al. |
| 6,797,217 B2 | 9/2004 | McCrea et al. |
| 6,800,089 B1 | 10/2004 | Wang |
| 6,802,859 B1 | 10/2004 | Pazienza et al. |
| 6,805,702 B1 | 10/2004 | Chen et al. |
| 6,805,703 B2 | 10/2004 | McMorrow |
| 6,805,704 B1 | 10/2004 | Hoyns |
| 6,805,705 B2 | 10/2004 | Hong et al. |
| 6,805,706 B2 | 10/2004 | Solovay et al. |
| 6,805,707 B1 | 10/2004 | Hong et al. |
| 6,805,709 B1 | 10/2004 | Schaldach et al. |
| 6,805,898 B1 | 10/2004 | Wu et al. |
| 6,808,533 B1 | 10/2004 | Goodwin et al. |
| 6,814,749 B2 | 11/2004 | Cox et al. |
| 6,818,013 B2 | 11/2004 | Mitelberg et al. |
| 6,818,014 B2 | 11/2004 | Cox et al. |
| 6,818,015 B2 | 11/2004 | Hankh et al. |
| 6,818,247 B1 | 11/2004 | Chen et al. |
| 6,821,291 B2 | 11/2004 | Bolea et al. |
| 6,821,292 B2 | 11/2004 | Pazienza et al. |
| 6,821,293 B2 | 11/2004 | Pinchasik |
| 6,830,638 B2 | 12/2004 | Boylan et al. |
| 6,833,004 B2 | 12/2004 | Ishii et al. |
| 6,843,802 B1 | 1/2005 | Villalobos et al. |
| 6,849,086 B2 | 2/2005 | Cragg |
| 6,852,124 B2 | 2/2005 | Cox et al. |
| 6,858,037 B2 | 2/2005 | Penn et al. |
| 6,860,898 B2 | 3/2005 | Stack et al. |
| 6,860,900 B2 | 3/2005 | Clerc et al. |
| 6,863,684 B2 | 3/2005 | Kim et al. |
| 6,866,805 B2 | 3/2005 | Hong et al. |
| 6,875,227 B2 | 4/2005 | Yoon |
| 6,878,162 B2 | 4/2005 | Bales et al. |
| 6,881,221 B2 | 4/2005 | Golds |
| 6,881,222 B2 | 4/2005 | White et al. |
| 6,881,223 B2 | 4/2005 | Penn et al. |
| 6,887,264 B2 | 5/2005 | Penn et al. |
| 6,896,696 B2 | 5/2005 | Doran et al. |
| 6,896,697 B1 | 5/2005 | Yip et al. |
| 6,896,698 B2 | 5/2005 | Rolando et al. |
| 6,899,729 B1 | 5/2005 | Cox et al. |
| 6,908,624 B2 | 6/2005 | Hossainy et al. |
| 6,911,041 B1 | 6/2005 | Zscheeg |
| 6,916,336 B2 | 7/2005 | Patel et al. |
| 6,920,677 B2 | 7/2005 | Dolan et al. |
| 6,955,723 B2 | 10/2005 | Pacetti et al. |
| 6,979,348 B2 | 12/2005 | Sundar |
| 7,004,966 B2 | 2/2006 | Edwin et al. |
| 2001/0000043 A1 | 3/2001 | Israel et al. |
| 2001/0005793 A1 | 6/2001 | Brenneman |
| 2001/0016767 A1 | 8/2001 | Wilson et al. |
| 2001/0016768 A1 | 8/2001 | Wilson et al. |
| 2001/0027339 A1 | 10/2001 | Boatman et al. |
| 2001/0037138 A1 | 11/2001 | Wilston et al. |
| 2002/0002396 A1 | 1/2002 | Fulkerson |
| 2002/0002399 A1 | 1/2002 | Huxel et al. |
| 2002/0042650 A1 | 4/2002 | Vardi et al. |
| 2002/0045933 A1 | 4/2002 | Jang |
| 2002/0111672 A1 | 8/2002 | Kim et al. |
| 2002/0156524 A1 | 10/2002 | Ehr et al. |
| 2002/0183831 A1 | 12/2002 | Rolando et al. |
| 2002/0183832 A1 | 12/2002 | Penn et al. |
| 2002/0193866 A1 | 12/2002 | Saunders |
| 2002/0198593 A1 | 12/2002 | Gomez et al. |
| 2003/0004567 A1 | 1/2003 | Boyle et al. |
| 2003/0024534 A1 | 2/2003 | Silvestri et al. |
| 2003/0028240 A1 | 2/2003 | Nolting et al. |
| 2003/0036793 A1 | 2/2003 | Richter et al. |
| 2003/0045925 A1 | 3/2003 | Jayaraman |
| 2003/0050690 A1 | 3/2003 | Kveen et al. |
| 2003/0077310 A1 | 4/2003 | Pathak et al. |
| 2003/0083734 A1 | 5/2003 | Friedrich et al. |
| 2003/0105511 A1 | 6/2003 | Welsh et al. |
| 2003/0105513 A1 | 6/2003 | Moriuchi et al. |
| 2003/0114919 A1 | 6/2003 | McQuiston et al. |
| 2003/0125799 A1 | 7/2003 | Limon |
| 2003/0139796 A1 | 7/2003 | Sequin et al. |
| 2003/0139803 A1 | 7/2003 | Sequin et al. |
| 2003/0144726 A1 | 7/2003 | Majercak et al. |
| 2003/0144731 A1 | 7/2003 | Wolinsky et al. |
| 2003/0149469 A1 | 8/2003 | Wolinsky et al. |
| 2003/0158596 A1 | 8/2003 | Ikeuchi et al. |

FOREIGN PATENT DOCUMENTS

| | | |
|---|---|---|
| DE | 299 04 817 U1 | 5/1999 |
| DE | 199 06 956 A 1 | 8/2000 |
| DE | 199 37 638 A 1 | 5/2001 |
| EP | 0 183 372 | 10/1984 |
| EP | 0 350 302 | 1/1990 |
| EP | 0 378 151 A2 | 7/1990 |
| EP | 0 540 290 A2 | 10/1991 |
| EP | 0 540 290 A2 | 5/1993 |
| EP | 0 621 015 A1 | 10/1994 |
| EP | 0 797 963 A2 | 1/1997 |
| EP | 0 792 627 A2 | 3/1997 |
| EP | 0 945 107 A2 | 1/1999 |
| EP | 1 088 528 A1 | 4/2001 |
| EP | 1 093 771 A2 | 4/2001 |
| EP | 1 208 814 A2 | 9/2001 |
| EP | 1 151 730 A2 | 11/2001 |
| EP | 1 197 188 A2 | 4/2002 |
| EP | 1 290 984 A2 | 12/2003 |
| FR | 2 758 253 A1 | 7/1998 |
| JP | 2002-102251 | 4/2002 |
| JP | 2002-345971 | 12/2002 |
| WO | WO 91/13384 | 9/1991 |
| WO | WO 92/11824 | 7/1992 |
| WO | WO 93/22986 | 11/1993 |
| WO | WO 94/04096 | 3/1994 |
| WO | WO 94/21196 | 9/1994 |
| WO | WO 97/07751 | 3/1997 |
| WO | WO 97/10011 | 3/1997 |
| WO | WO 98/19628 A1 | 5/1998 |
| WO | WO 99/02105 A1 | 1/1999 |
| WO | WO 99/40876 | 8/1999 |
| WO | WO 99/62430 | 12/1999 |
| WO | WO 00/09041 | 2/2000 |
| WO | WO 00/44309 A2 | 8/2000 |
| WO | WO 00/45742 | 8/2000 |
| WO | WO 01/76508 A2 | 10/2001 |
| WO | WO 02/19948 A2 | 3/2002 |

OTHER PUBLICATIONS

PCT Notification of Transmittal of the International Search Report, PCT International Search Report mailed Mar. 9, 2005 for PCT/US04/31898 (Filed Sep. 29, 2004).

Supplementary European Search Report for EP 03 77 6570, completed Apr. 30, 2007, mailed on May 14, 2007.

U.S. Appl. No. 08/246,320, filed May 19, 1994, Burnmeister et al.

D.H. Kim et al., Evaluation of the Biodurability of Polyurethane Covered Stent Using a Flow Phantom, Korean J. Radiology, Jun. 2001: 2:75-79.

* cited by examiner

STENT WITH GEOMETRY DETERMINATED FUNCTIONALITY AND METHOD OF MAKING THE SAME

FIELD OF INVENTION

The present invention relates generally to medical devices directed to the prevention of luminal occlusion, and more particularly to stents and methods for making and utilizing these stents in the treatment of both benign and malignant conditions wherein the functionality of the stents is determined by geometrical variability of the scaffolding and concomitant interstices.

BACKGROUND OF THE INVENTION

Stents are devices that are inserted into a vessel or passage to keep the lumen open and prevent closure due to a stricture, external compression, or internal obstruction. In particular, stents are commonly used to keep blood vessels open in the coronary arteries and they are frequently inserted into the ureters to maintain drainage from the kidneys, the bile duct for pancreatic cancer or cholangiocarcinoma or the esophagus for strictures or cancer. Vascular as well as not vascular stenting has evolved significantly; unfortunately there remain significant limitations with respect to the technology for producing stents suitable to various portions of a patient's anatomy.

Historically, in order to provide a stent with varying characteristics, the stent had to be manufactured from multiple materials, at least one for each characteristic desired. As a result, many of these stents are woven from two or more metals having differing shape-memories for example. Unfortunately, braided stents are vulnerable to premature obsolescence. Moreover, providing multiple material types in a single stent may lead to inconsistent characteristics along the surface area of the stent. This is particularly undesirable when the stent is to be placed in vascular or nonvascular lumens that have been occluded for one reason or another. The stent needs to be stiffer in some regions while more flexible in others. Therefore, there remains an existing need for a therapeutic stent that can have varying characteristics along its surface area while being stamped, not braded, from a single base material. Moreover, there is a need for such a therapeutic stent where the relative hardness, softness, flexibility, stiffness and radial force can be modified as a function of geometric considerations rather than material considerations. In particular, there is a need for a stent that is divided into zones so as to allow the stent to have predetermined characteristics in one zone and could conceivably have drastically different characteristics in an adjacent zone so as to allow for stents that can be tailored to anatomical lumens in general and the particular lumen topography of a specific patient in particular.

SUMMARY OF EXEMPLARY EMBODIMENTS

It is a principal purpose of the present invention to provide a stent, in accordance with an exemplary embodiment of the present invention, which combines many of the excellent characteristics of both silicone and metal stents while eliminating the undesirable ones. In particular, it is an objective of a preferred embodiment in accordance with the present invention to provide a stent that is easily installed, yet in alternative embodiments, removable. Moreover the stent in accordance with this embodiment of the present invention would not cause material infections and may be capable of reducing infection. Therefore, a principal objective of a preferred embodiment in accordance with the present invention is to provide a prosthesis that is suitable for both permanent and temporary use while being easy to insert, reposition and remove.

A principal objective of a preferred embodiment of the present invention is to provide a stent that may be stamped from preferably a single material that is capable of maintaining its axial working length when radially compressed. To this end, the stent does not have a seam that could aggravate luminal tissue. In particular, a stent in accordance with the present invention is formed using a tool that molds the stents outer contour as well as its interstices.

It is yet another objective of an exemplary embodiment of the present invention to provide a stent that can be indicated for the treatment of benign and malignant disease and improve the way clinicians treat malignant obstructions.

Still another objective of the present invention is to provide a stent and method for installing the stent that is economical and suitable for routine purposes. Moreover, the stent will have minimal migration, cause minimal tissue granulation, will not foreshorten after deployment and mucociliary clearance will not be problematic.

Yet another objective of an exemplary embodiment in accordance with the present invention is to provide a prosthesis that will have superior internal to external diameter ratio, superior radial force with dynamic expansion, while being suitable for use in pediatric and adult patients with malignant and benign disease.

A principal objective of an exemplary stent in accordance with the present invention is to provide a family of stents where the relative hardness/softness of regions of the stent can differ from other regions of the stent to provide additional patient comfort and resistance to radial forces.

An additional objective in accordance with an exemplary embodiment is to provide a family of stents with novel interstice configurations that facilitate flexibility, durability and/or proper installation.

Still another objective of a preferred embodiment of the present invention is to provide a self-expanding stent have the above benefits that also defines a plurality of apertures at the termini of the stent for, inter alia, removal of the stent.

Further objectives, features and advantages of the invention will be apparent from the following detailed description taken in conjunction with the accompanying drawings.

DETAILED DESCRIPTION OF AN EMBODIMENT

A preferred embodiment of the stent, in accordance with the present invention, provides a stent that prevents epithelialization of the stent and is not subject to premature elongation and foreshortening but is capable of engaging the desired implantation location. The stent also retains its axial length while undergoing radial compression.

The stent is preferably formed from a composite material selected from the group consisting essentially of Ni, C, Co, Cu, Cr, H, Fe, Nb, O, Ti and combinations thereof. The composite material is generally formed into a compressed tube from which the stent is etched and is formed on a suitable shaping device to give the stent the desired external geometry. Both the synthetic collar techniques and in vitro valuation techniques show the remarkable ability of stents in accordance with the present invention to convert acting force into deformation work absorbed by the angled structure, which prevents excessive scaffolding stress and premature material fatigue and accelerated obsolescence.

Though one skilled in the stent engineering art, once apprised of the present application, would be able to manufacture a stent consistent with the present invention by other methods, a preferred method of manufacturing such stents follows. As stated above a composite material is selected and a blank is formed there from. The blank is preferably laser etched and the etch work is generally verified for accuracy using visual recording microscopy. Dimensional measurements are taken to ensure strut thickness, segment angles, zone placement, etc. Moreover, the stent is preferably formed on a shaping tool that has substantially the desired contour of the external stent dimensions.

In the event the stent is to be shaped to the dimensions of a particular lumen, optical photography and/or optical videography of the target lumen may be conducted prior to stent formation. The geometry of corresponding zones and connector regions of the stent then can be etched and formed in accordance with the requirements of that target lumen. For example, if the stent were designed for the trachea, which has a substantially D shaped lumen and additionally the middle zones needed to be softer than the end zones, the stent could be designed to those specifications. In particular, if the topography of the trachea of a particular patient is captured optically and the appropriate dimension provided, a patient specific prosthesis could be engineered. These techniques can be adapted to other non-vascular lumen but is very well suited for vascular applications where patient specific topography is a function of a variety of factors such as genetics, lifestyle, etc.

It should be pointed out that unlike the use of differing shape memory materials to change regions of a stent, stents in accordance with the present invention can take on an infinite number of characteristic combinations as zones and segments within a zone can be modified by changing angles, segment lengths and segment thicknesses during the etching and forming stages of stent engineering or during post formation processing and polishing steps. Moreover, by modifying the geometry of the connectors between zones, addition functionality may be achieved.

Figure 1:
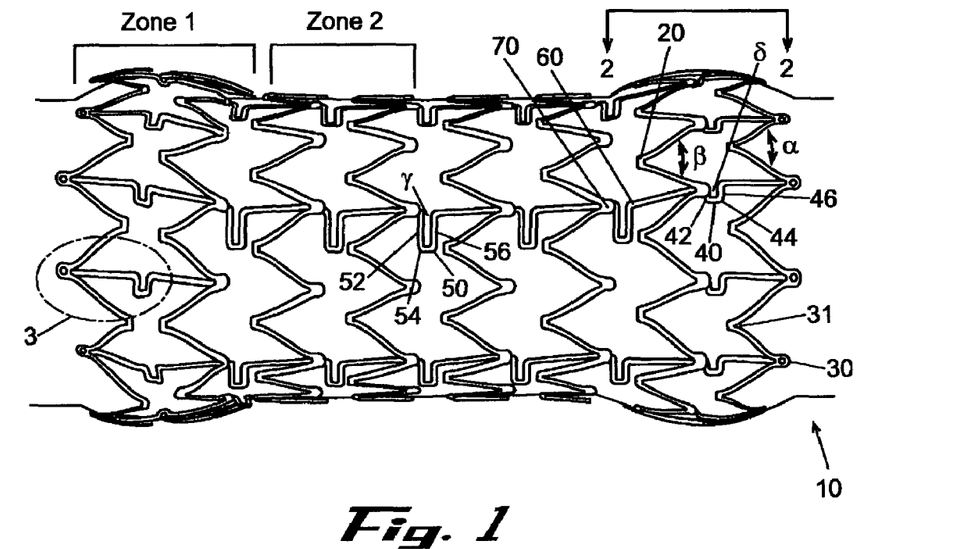
FIG. 1 shows a side perspective view of an exemplary stent in accordance with the present invention.
Figure 2:
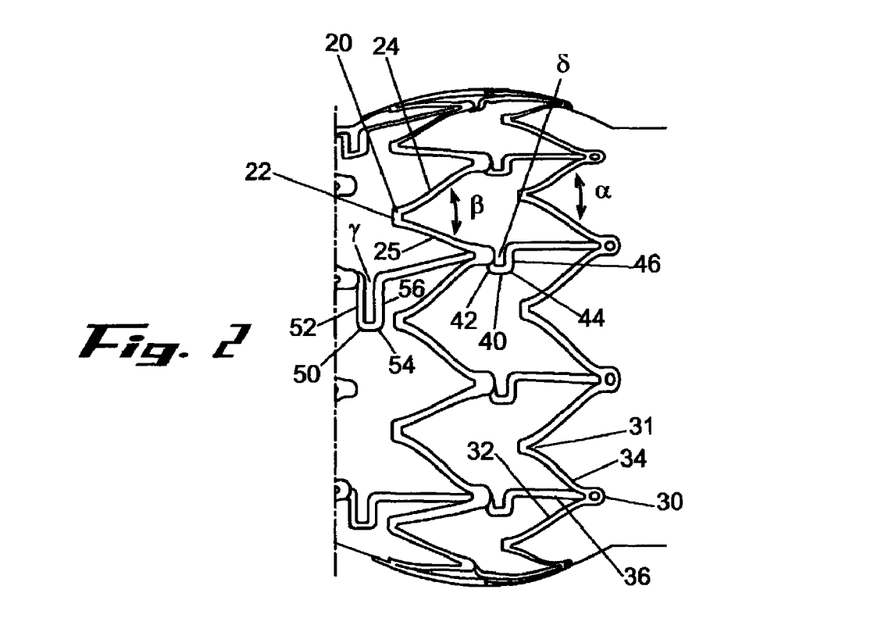
FIG. 2 shows a side perspective view of a single zone of the stent shown in FIG. 1.
Figure 3:
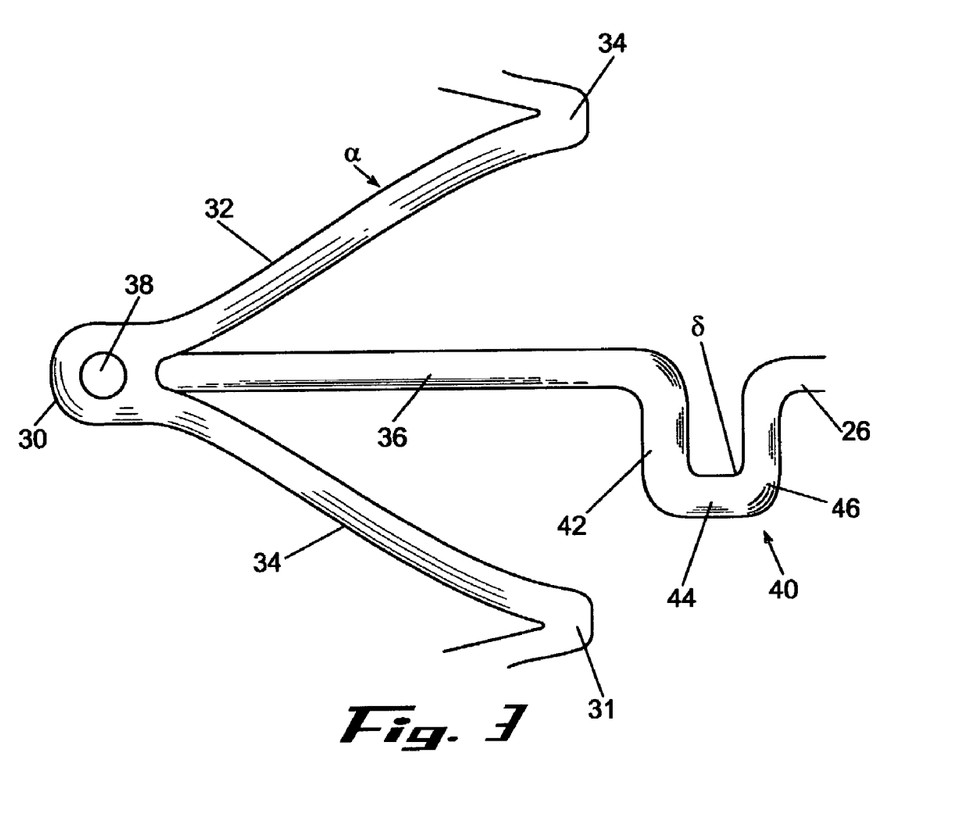
FIG. 3 shows an enlarged perspective view of the interstices of an exemplary zone as shown in FIG. 2.
Figure 4:
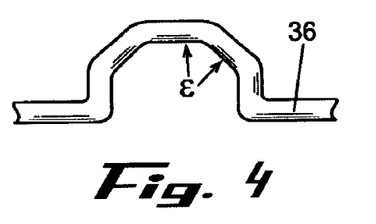
FIG. 4 shows an enlarged perspective view of the interstices of an exemplary zone as shown in FIG. 2 showing an alternative octagonal connection member.
Figure 5:
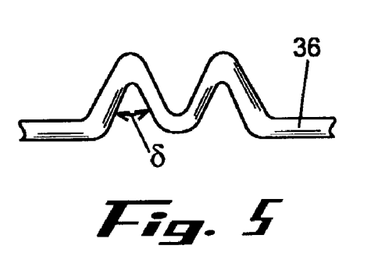
FIG. 5 shows an enlarged perspective view of the interstices of an exemplary zone as shown in FIG. 2 showing an alternative omega shaped connection member.
Figure 6:
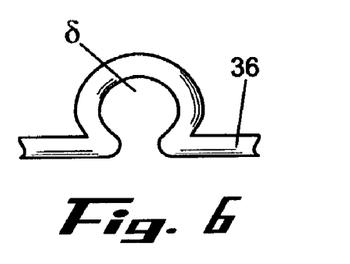
FIG. 6 shows an enlarged perspective view of the interstices of an exemplary zone as shown in FIG. 2 showing an alternative M shaped connection member.
Figure 7:
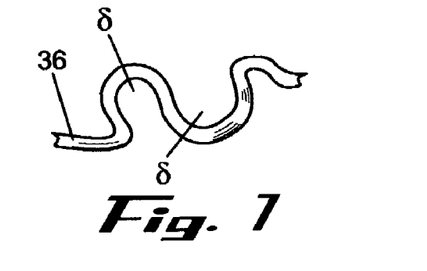
FIG. 7 shows an enlarged perspective view of the interstices of an exemplary zone as shown in FIG. 2 showing an alternative S shaped connection member.

Exemplary stents 10 in accordance with the present invention are shown in FIGS. 1-3 showing the preferred interstice geometry. Not shown are a wide variety of interstice geometries that are also acceptable alternatives to the preferred, namely, U, V, W, Z, S and X geometries to name a few.

The stent 10 also is formed of memory metal and preferably has unique geometrical interstices that are laser etched therein. However, other conventional ways of forming interstices in unitary stents, though not equivalent are contemplated, may be employed and would be within the skill set of one in the art.

It cannot be overemphasized, however, that this does not mean the knowledge that changes in the geometry of interstices affect stent functionality is currently known in the art. To the contrary, the present inventors discovered the interrelation between interstice geometry, width, length and relative resistance to torsional stress and radial force. In fact, it can be said that the stent 10 has circumferential bands extending perpendicularly with respect to the luminal device's longitudinal axis. These bands are referred to generally as zones. A connector 50 connects these bands to one another; the connector 50 is an additional means for adjusting stent functionality. In particular, the connector 50 defines a substantially U shaped member, but could define other geometries such as U, V, W, Z, S and X to name a few.

In a standard orientation, as shown particularly in FIG. 1, the substantially U-shape connector comprises preferably two leg members 52 & 56 and a crossing member 54 that connects with and extends perpendicularly at preferably 90° angles with respect to the leg members 52 & 56. It must be noted that alternative angles may be provided without departing materially from the invention. The present inventors discovered that if you modify the length of the crossing member 54 and/or the leg members 52 & 56 and/or the angle γ at which the crossing member 54 and the leg members 52 & 56 intersect, the relative hardness/softness, radial force and/or flexibility of the stent 10 could be modified. The angles γ can be modified at varying acute angles short of 90° or varying obtuse angles greater than 90°. The incremental changes correspondingly change certain characteristics of the stent 10. As a result, different zones of the stent 10 can be given different rigidities to improve patient comfort and for example, in airway stents, to facilitate luminal patency. Moreover, various anatomical lumens may need different degrees of stent rigidity. As a result, stents 10 in accordance with the present invention can be manufactured to exacting specifications to contour properly to various lumens in a patient's anatomy, which may need varying levels of structural support from the medical appliance.

Figure 10:
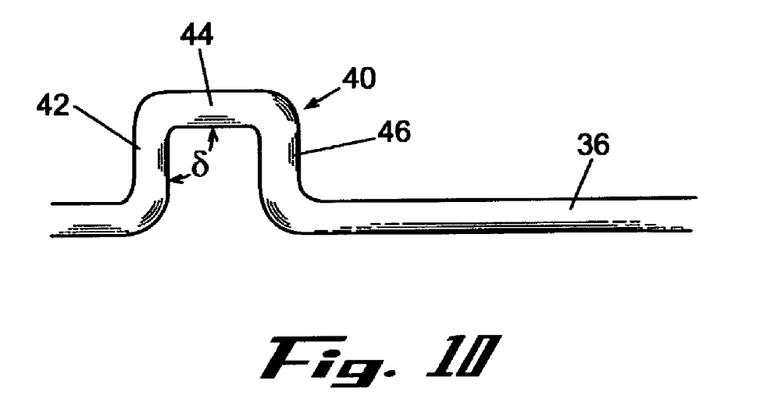
FIG. 10 shows an enlarged perspective view of an exemplary connector wherein the connector is oriented closer to one zone than another.
Figure 11:
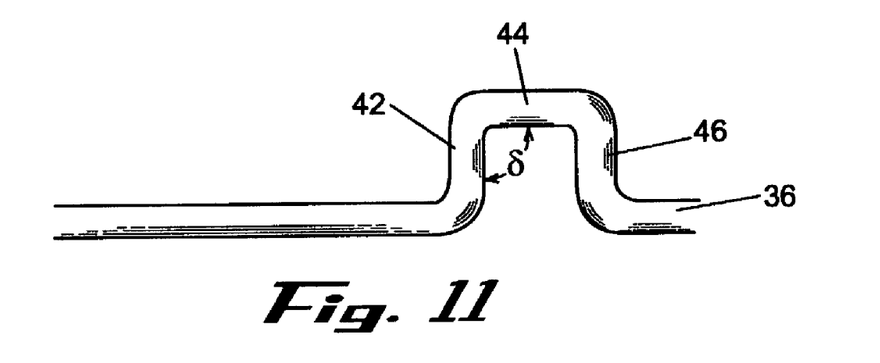
FIG. 11 shows an enlarged perspective view of an exemplary connector wherein the connector is oriented closer to the opposite zone as the connector shown in FIG. 10.
Figure 12:
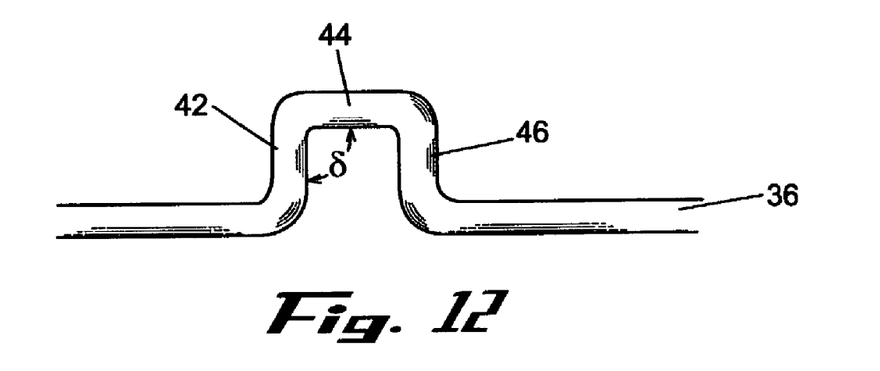
FIG. 12 shows an enlarged perspective view of an exemplary connector wherein the connector is oriented substantially equidistant between two zones.

As depicted in FIGS. 10-12, by adjusting the distance between the connector 50 and for examples Zones 2 and 3 between which connector 50 resides, the way in which the stent reacts to strain can be modified. By way of non-limiting example, if the connector 40 is oriented closer to zone 3 than to zone 2, the stent will be less flexible and be able to withstand greater radial force. Alternatively, if the connector is equidistant between Zones 2 and 3, the stent will be more flexible and be able to withstand less radial force. Please note that these differences are relative to a neutrally located connector 40. The behavior is a function of distance and as a result varies along a continuum with respect to the connector's orientation between the medium between zones and the tip of each zone. Moreover, within by varying the number of connectors 40 that connect the zones to one another, functionality can be impacted. In particular, the fewer the number of connectors connecting the zones the more torsional flexibility the stent will have. The converse will generally hold true with respect to a greater number of connectors.

Referring now to FIG. 2, stent 10 is shown having several bands within a zone forming substantially arrow shaped regions. In particular, each arrow shaped band preferably comprises a forward angle β and a rear angle α. The forward angle β is formed by the intersection of two legs 24 & 25. Legs 24 & 25 connect at first ends 26 & 27 to form the head 22 of angle β. Second ends 28 & 29 of legs 24 & 25 terminate at connectors 40. Connector 40 connects the legs 24 & 25 of forward angle β to the legs 32 & 34 of rear angle α via intermediary leg 36. Where legs 32, 34 & 36 connect is the head 30, which defines an aperture 38 for installing suture.

Connector 40, which serves a similar purpose as connector 50 also has a crossing member 44 that connects leg members 42 & 46 at a predetermined angle δ. As discussed above, since form follows function for stents prepared through this novel method, by changing the degrees of angles α, β, δ & γ, stent characteristics can be modified. Moreover, by changing the leg lengths of all the previously discussed legs or individual legs separately, additional stent characteristics can be obtained. The beauty of this system is that the desired characteristics can be determined prior to forming the stent and by staying within certain forming parameters, the stent can be formed, crimped, delivered and deployed with confidence that the desired functionality with result. This is important in light of the fact that both vascular and nonvascular lumen have unique topography. As a result, methods and devices in accordance with the present invention usher in the ability to tailor prosthesis to anatomical tissue in general and particular patient anatomy in particular.

The U shaped connectors 40 & 50 have a crossing member and at least two leg members, respectively. The present inventors discovered that if you increase/decrease the length of leg members and/or increase/decrease the length of crossing members and/or vary the angle at which crossing members and leg members intersect, you affect the functionality of the stent. In particular, the shorter the length of the leg members, the less flexibility available in that portion of the stent. Taking particular note of FIG. 3, by way of example only, if you want to decrease the amount of torsional flexibility of the stent 10, you would have to modify the connector 40 so that the legs 42 & 46 are longer than shown and that the angle δ formed by legs 42 & 46 and crossing member 44, respectively, is slightly greater than 90°. Alternatively, the length of the crossing member 44 can impact the functionality of the stent as well. The stent can be made more rigid by shortening crossing member 44 or the stent may be made more flexible by lengthening crossing member 44. It should be noted that the combination of the changes of leg lengths, crossing member lengths, angle variations, shapes and number of connectors provide the stent with the ability to conform to specific lumens in the anatomy of a patient. The result is a form fitting medical prosthesis that may be tailored to specific anatomical lumens in general and to the anatomical lumens of an individual patient in particular.

In a preferred embodiment, the modification of interstice geometries and manipulation of the U shaped connection member to achieve variable stent functionality is provided. The rigidity of the stent scaffolding or interstice matrix along with the torsionality of the stent itself is principally a function of these modifications. In an exemplary embodiment, the stents relative flexibility can be rated soft, medium or hard based on the degree of flex and torsionality. The less torsionality and flex in the stent the harder the stent is rated.

An exemplary stent in accordance with the present invention with relatively great torsionality and radial flexibility would be rated soft. An exemplary soft rated stent comprises distance between U shaped connectors of about 4.5 μm in the compressed state (i.e., contracted in the 3 mm tube subject to laser etching). Moreover, the length of the crossing member is preferably about 1.0 μm. The lengths of the leg members are preferably about 1.5 μm in length. Additionally the leg members may further comprise feet that attached to the remainder of the stent scaffolding. The feet can be adjusted from a standard length of about 0.25 μm to further adjust the characteristics of the stent. There is additionally a substantially rectangular member incorporated in the U shaped connector with similar capacity for variability. The variability factors and results of modifying the dimensions of the substantially rectangular members are similar to those evinced by leg length dimensional modifications.

Figure 8:
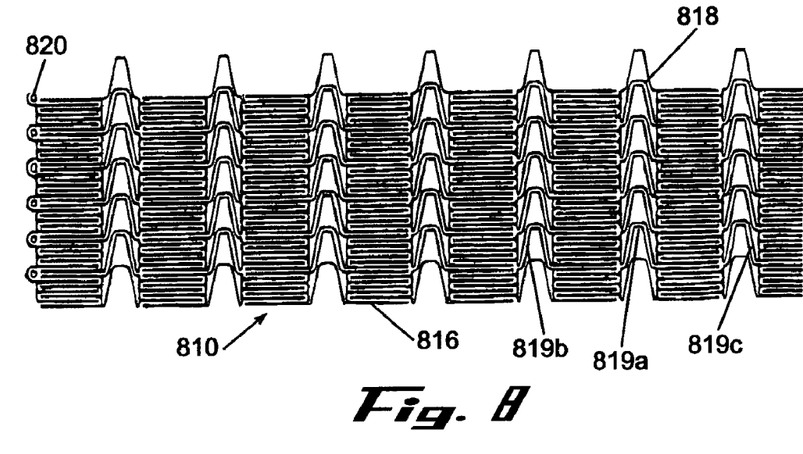
FIG. 8 shows a magnified view of the scaffolding and interstice topology of the medical appliance shown in FIG. 1.
Figure 9:
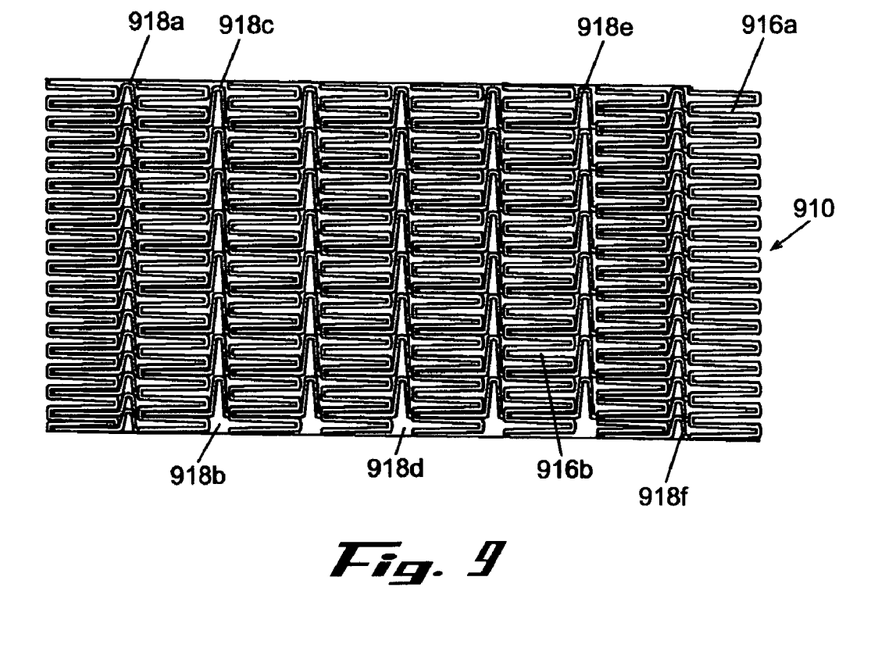
FIG. 9 shows a magnified portion of the scaffolding and interstice topology of the medical appliance of FIG. 1, showing how modifications in geometric dimensions affect functionality.

Referring now to FIGS. 8 and 9, where like numerals refer to like parts, luminal stent 810 is shown having substantially U shaped connectors 818 having a crossing member 819a and at least two leg members 819b-c respectively. The present inventors discovered that if you increase/decrease the length of leg member 819b and/or 819c, increase/decrease the length of crossing member 819a, and/or vary the angle at which crossing member 819a and leg members 819b-c intersect, you affect the functionality of the stent. In particular, the shorter the length of leg members 819a-b the less flexibility available in that portion of the stent. Taking particular note of FIG. 9, by way of example only, if you want to decrease the amount of torsional flexibility of the luminal stent 910, you would have to modify the desired portion of the stent to resemble 918f. However, if you want a stiffer appliance 910, you would have a configuration analogous to that of 918a.

By way of example, but not to be construed in any way as limiting, the softness index or relative flexibility can be increase by increasing the various lengths discussed above. For example, by increasing the length of the legs and crossing members of the U shaped connector, flexibility increases. However, with respect to the distance between U shaped members and distance between interstices in a preferred stent embodiment, there is an inverse correlation between length and softness. This relative softness/hardness indexing as a corollary of interstice dimensions is a novel aspect of preferred embodiment of the present invention. As a practical rule of thumb, longer leg lengths coupled with acute angles provide for greater flexibility. Conversely, shorter leg lengths and more obtuse angles provide more rigidity. By way of non-limiting example, a U shaped connector with short legs deviating from the crossing member at angles greater than 90°, will be extremely rigid and resistant to torsional strain as compared to a U shaped connector with longer legs diverging from the crossing member at angles less than 90°.

In addition to the length and spacing differences, the interstices themselves may define various shapes that by their very nature afford novel functionality to the stent. The changes of functionality, however, are more a function of the dimensional differences of the various shapes rather than a function of the shapes themselves. Therefore, it is important to keep in mind that the dimensional differences discussed in the previous paragraph are determinative of the functionality accorded the stent by the varying interstice geometries. It is for this reason that one of ordinary skill in the art, after being apprised of the present invention, would be able to conceive of a number of interstice geometries to satisfy certain functionality criteria by keeping certain dimensional parameters constant.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A medical appliance for placement within a portion of the anatomy of a patient, the appliance comprising:
    a scaffolding, the scaffolding configured to define a substantially cylindrical member having a distal end and a proximal end and extending longitudinally there between, forming a lumen there through, such that when pressure is exerted along varying points of the longitudinal extension of the appliance, the appliance does not undesirably foreshorten or elongate
    said scaffolding including:
        a plurality of expandable circumferential bands, each of the circumferential bands having a plurality of angularly extending legs with interconnected ends defining a plurality of peaks and valleys, wherein the legs have approximately equal lengths within each of the circumferential bands, and
        a plurality of connectors coupled to respective peaks and/or valleys of each adjacent pair of the circumferential bands, each of the connectors including a flexible portion that is configured to be positioned between peaks and/or valleys of adjacent ones of the circumferential bands when the scaffolding is compressed, wherein each flexible portion includes a pair of connector leg members and a crossing member that connects the leg members at a predetermined angle, and wherein the peaks of at least two adjacent circumferential bands are connected by the connectors extending therebetween to define a plurality of arrow shaped regions.

2. The medical appliance of claim 1, wherein along the longitudinal extension of the appliance, the scaffolding forms geometrical patterns.

3. The medical appliance of claim 2, wherein the scaffolding further comprises a coating coupled with the scaffolding, the coating of sufficient thickness to prevent the medical appliance from becoming epithelialized when installed in the desired portion of the patient's anatomy.

4. The medical appliance of claim 3, wherein the coating does not inhibit flexing or radial expansion of the medical appliance.

5. The medical appliance of claim 4, wherein the coating is coupled with the medical appliance about the proximal and distal ends thereof.

6. The medical appliance of claim 2, wherein the dimensions of the scaffolding geometry determine torsionality of the medical appliance.

7. The medical appliance of claim 2, wherein the geometrical patterns are substantially U-shaped.

8. The medical appliance of claim 1, wherein the scaffolding is formed of a memory capable alloy.

9. The medical appliance of claim 8, wherein the scaffolding is electro polished.

10. The medical appliance of claim 1, wherein near the distal and proximal ends of the scaffolding the medical appliance further comprise a plurality of flanges that define apertures there through.

11. The medical appliance of claim 1, wherein the flexible portion further comprises a rectangular detent extending from a connector leg thereof.

12. The medical appliance of claim 1, wherein the length of the connector leg members and the degree of the angle at which the connector legs extend from the crossing member determines the relative flexibility of the medical appliance.

13. The medical appliance of claim 12, wherein the angle at which the connector leg members extend from the crossing member is 90° or less.

14. The medical appliance of claim 13, wherein the medical appliance is relatively flexible.

15. The medical appliance of claim 1, further comprising an additional distal end wherein the medical appliance forms a substantially Y-shape.

16. The medical appliance of claim 15, wherein along the longitudinal extension of the appliance, the scaffolding forms geometrical patterns.

17. The medical appliance of claim 16, wherein the scaffolding further comprises a coating coupled with the scaffolding, the coating of sufficient thickness to prevent the medical appliance from becoming epithelialized when installed in the desired portion of the patient's anatomy.

18. The medical appliance of claim 17, wherein the dimensions of the scaffolding geometry determine torsionality of the medical appliance.

19. The medical appliance of claim 18, wherein the scaffolding is electropolished.

20. The medical appliance of claim 17, wherein the scaffolding is formed of a memory capable alloy.

21. The medical appliance of claim 17, wherein near the distal and proximal ends of the scaffolding the medical appliance further comprise a plurality of flanges that define apertures there through.

22. The medical appliance of claim 15, wherein the connector includes a crossing member and a plurality of connector leg members extending from the crossing member.

23. The medical appliance of claim 22, wherein the connector further comprises a rectangular detent extending from a connector leg thereof.

24. The medical appliance of claim 22, wherein the length of the connector leg members or the degree of the angle at which the connector legs extend from the crossing member positively contributes to the relative flexibility of the medical appliance.

25. The medical appliance of claim 24, wherein the angle at which the connector leg members extend from the crossing member is 90° or less.

26. The medical appliance of claim 25, wherein the medical appliance is relatively flexible.

27. The medical appliance of claim 15, wherein the geometrical patterns are substantially U-shaped.

28. The medical appliance of claim 1, wherein at least two circumferential bands include at least some connectors that connect the peak of one of the circumferential bands with the valley of an adjacent one of the circumferential bands.

29. The medical appliance of claim 28, wherein each of the connectors includes at least one straight longitudinal portion that extends from the flexible portion, between adjacent legs of the adjacent one of the circumferential bands, and connects to the valley.

30. The medical appliance of claim 28, wherein the plurality of arrow shaped regions are located at the proximal or distal ends of the scaffolding, and wherein the at least two circumferential bands having connectors connecting the peaks and valleys are located at an end of the scaffolding opposite that of the arrow shaped regions.

31. The medical appliance of claim 1, wherein said flexible portion extends circumferentially to abut a circumferentially adjacent flexible portion.

32. A method of treating a patient suffering from luminal irregularities, comprising the steps of:
providing a medical appliance comprising a scaffolding, the scaffolding configured to define a substantially cylindrical member having a distal end and a proximal end and extending longitudinally there between, forming a lumen there through, along the longitudinal extension of the appliance the scaffolding forms geometrical patterns formed by angles, wherein the angles determine the relative flexibility of the medical appliance such that the appliance conforms to the topography of a target lumen and when pressure is exerted along varying points of the longitudinal extension of the appliance, the appliance does not undesirably foreshorten or elongate,
said scaffolding including:
a plurality of expandable circumferential bands, each of the circumferential bands having a plurality of angularly extending legs with interconnected ends defining a plurality of peaks and valleys, wherein the legs have approximately equal lengths within each of the circumferential bands, and
a plurality of connectors coupled to respective peaks and/or valleys of each adjacent pair of the circumferential bands, each of the connectors including a flexible portion that is configured to be positioned between peaks and/or valleys of adjacent ones of the circumferential bands when the scaffolding is compressed, wherein each flexible portion includes a pair of connector leg members and a crossing member that connects the leg members at a predetermined angle, and wherein the peaks of at least two adjacent circumferential bands are connected by the connectors extending therebetween to define a plurality of arrow shaped regions;
installing the medical appliance in a preferred location of the anatomy of the patient; and
activating the expansion of the medical appliance in the desired location.

33. The method of claim 32, wherein the preferred location is a non-vascular lumen.

34. The method of claim 33, further comprising the step of removing the medical appliance from the anatomy of the patient.

35. The method of claim 33, wherein the medical appliance further comprises anti-microbial agents coupled therewith.

36. The method of claim 33, wherein the medical appliance further comprises chemotherapeutic agents coupled therewith.

37. The medical appliance of claim 32, further comprising an additional distal end wherein the medical appliance forms a substantially Y-shape.

38. A medical appliance comprising:
a plurality of expandable circumferential bands, each of the circumferential bands having a plurality of angularly extending legs with interconnected ends defining a plurality of peaks and valleys, wherein the legs have approximately equal lengths within each of the circumferential bands; and
a plurality of connectors coupled to respective peaks and/or valleys of each adjacent pair of the circumferential bands, each of the connectors including a flexible portion that is configured to be positioned between peaks and/or valleys of adjacent ones of the circumferential bands when the medical appliance is compressed,
wherein said flexible portion is further configured to extend circumferentially to abut a circumferentially adjacent flexible portion when the medical appliance is compressed, and wherein each flexible portion includes a pair of connector leg members and a crossing member that connects the leg members at a predetermined angle, and wherein the peaks of at least two adjacent circumferential bands are connected by the connectors extending therebetween to define a plurality of arrow shaped regions.

* * * * *